(12) United States Patent
Guerra (10) Patent No.: US 7,628,792 B2
(45) Date of Patent: Dec. 8, 2009

(54) BILATERAL FOOT JAWS

(75) Inventor: Paul Guerra, Boulder, CO (US)

(73) Assignee: Covidien AG, Neuhausen Am Rheinfall (CH)

( * ) Notice: Subject to any disclaimer, the term of this patent is extended or adjusted under 35 U.S.C. 154(b) by 357 days.

(21) Appl. No.: 11/232,410

(22) Filed: Sep. 22, 2005

(65) Prior Publication Data

US 2006/0079890 A1    Apr. 13, 2006

Related U.S. Application Data

(60) Provisional application No. 60/616,969, filed on Oct. 8, 2004.

(51) Int. Cl.
*A61B 18/14* (2006.01)

(52) U.S. Cl. ............... 606/51; 606/50; 606/52; 606/206; 606/207

(58) Field of Classification Search ............ 606/45, 606/48–52, 205–207
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |

(Continued)

FOREIGN PATENT DOCUMENTS

CA    2104423    2/1994

(Continued)

OTHER PUBLICATIONS

Int'l Search Report EP 05016399 dated Jan. 5, 2006.

(Continued)

*Primary Examiner*—Lee S Cohen
*Assistant Examiner*—Amanda Scott (57) ABSTRACT

A surgical instrument is provided and includes a drive rod assembly having a hollow shaft portion. A central shaft is slidably disposed in and axially aligned with the hollow shaft portion. The instrument may further include a handle assembly coupled to hollow shaft portion and the central shaft of the drive rod assembly. A pair of opposing jaw members each operatively associated with the distal end of the hollow shaft portion, the jaw members being movable relative to one another between a first position wherein the jaw members are disposed in spaced relation relative to one another and a second position wherein the jaw members are approximated towards one another. The instrument may further include a source of electrical energy connected to each jaw member for conducting energy therebetween.

19 Claims, 5 Drawing Sheets

U.S. PATENT DOCUMENTS

| | | | |
|---|---|---|---|
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,300,564 A | 11/1981 | Furihata | |
| 4,370,980 A | 2/1983 | Lottick | |
| 4,416,276 A | 11/1983 | Newton et al. | |
| 4,452,246 A | 6/1984 | Bader et al. | |
| 4,492,231 A | 1/1985 | Auth | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| D295,893 S | 5/1988 | Sharkany et al. | |
| D295,894 S | 5/1988 | Sharkany et al. | |
| 4,763,669 A | 8/1988 | Jaeger | |
| 4,827,929 A | 5/1989 | Hodge | |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,084,057 A | 1/1992 | Green et al. | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Xamiyama et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,211,655 A * | 5/1993 | Hasson | 606/205 |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,290,286 A | 3/1994 | Parins | |
| 5,304,203 A | 4/1994 | El-Mallawany et al. | |
| 5,308,357 A | 5/1994 | Lichtman | |
| 5,318,589 A | 6/1994 | Lichtman | |
| 5,324,289 A | 6/1994 | Eggers | |
| 5,330,471 A * | 7/1994 | Eggers | 606/48 |
| 5,334,183 A | 8/1994 | Wuchinich | |
| 5,334,215 A | 8/1994 | Chen | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,405,344 A * | 4/1995 | Williamson et al. | 606/1 |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,422,567 A | 6/1995 | Matsunaga | |
| 5,423,810 A | 6/1995 | Goble et al. | |
| 5,425,739 A | 6/1995 | Jessen | |
| 5,429,616 A | 7/1995 | Schaffer | |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A | 1/1996 | Riza | |
| 5,484,436 A | 1/1996 | Eggers et al. | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |
| 5,527,313 A | 6/1996 | Scott et al. | |
| 5,531,744 A | 7/1996 | Nardella et al. | |
| 5,536,251 A | 7/1996 | Evard et al. | |
| 5,540,684 A | 7/1996 | Hassler, Jr. | |
| 5,540,685 A | 7/1996 | Parins et al. | |
| 5,540,715 A | 7/1996 | Katsaros et al. | |
| 5,542,945 A | 8/1996 | Fritzsch | |
| 5,558,672 A | 9/1996 | Edwards et al. | |
| 5,562,699 A | 10/1996 | Heimberger et al. | |
| 5,569,241 A | 10/1996 | Edwardds | |
| 5,569,243 A | 10/1996 | Kortenbach et al. | |
| 5,571,100 A | 11/1996 | Goble et al. | |
| 5,573,424 A | 11/1996 | Poppe | |
| 5,573,534 A | 11/1996 | Stone | |
| 5,573,535 A | 11/1996 | Viklund | |
| 5,578,052 A | 11/1996 | Koros et al. | |
| 5,582,611 A | 12/1996 | Tsukagoshi et al. | |
| 5,585,896 A | 12/1996 | Yamazaki et al. | |
| 5,590,570 A | 1/1997 | LeMaire, III et al. | |
| 5,601,601 A | 2/1997 | Tal et al. | |
| 5,603,711 A | 2/1997 | Parins et al. | |
| 5,603,723 A | 2/1997 | Aranyi et al. | |
| 5,611,798 A | 3/1997 | Eggers | |
| 5,611,813 A * | 3/1997 | Lichtman | 606/205 |
| 5,626,578 A | 5/1997 | Tihon | |
| 5,626,609 A | 5/1997 | Zvenyatsky et al. | |
| 5,630,833 A | 5/1997 | Katsaros et al. | |
| 5,637,110 A | 6/1997 | Pennybacker et al. | |

| Patent | Date | Inventor |
|---|---|---|
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,958 A | 8/1998 | Yoon |
| 5,800,449 A | 9/1998 | Wales |
| 5,807,393 A | 9/1998 | Williamsom, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,876,401 A | 3/1999 | Schulze et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,935,126 A | 8/1999 | Riza |
| 5,944,718 A | 8/1999 | Dafforn et al. |
| 5,951,549 A | 9/1999 | Richardson et al. |
| 5,954,720 A | 9/1999 | Wilson et al. |
| 5,957,923 A | 9/1999 | Hahnen et al. |
| 5,961,514 A | 10/1999 | Long et al. |
| 5,976,132 A | 11/1999 | Morris |
| 5,984,939 A | 11/1999 | Yoon |
| 5,989,277 A | 11/1999 | LeMaire, III et al. |
| 6,004,335 A | 12/1999 | Vaitekunas et al. |
| 6,010,516 A | 1/2000 | Hulka et al. |
| 6,024,741 A | 2/2000 | Williamson et al. |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |

| | | | | | | |
|---|---|---|---|---|---|---|
| 6,458,128 | B1 | 10/2002 | Schulze | 7,207,990 B2 | 4/2007 | Lands et al. |
| 6,458,130 | B1 * | 10/2002 | Frazier et al. ............... 606/51 | D541,938 S | 5/2007 | Kerr et al. |
| 6,464,701 | B1 | 10/2002 | Hooven et al. | 7,223,265 B2 | 5/2007 | Keppel |
| 6,464,702 | B2 | 10/2002 | Schulze et al. | 7,232,440 B2 | 6/2007 | Dumbauld et al. |
| 6,464,704 | B2 | 10/2002 | Schmaltz et al. | 7,241,296 B2 | 7/2007 | Buysse et al. |
| 6,511,480 | B1 | 1/2003 | Tetzlaff et al. | 7,252,667 B2 | 8/2007 | Moses et al. |
| 6,527,771 | B1 | 3/2003 | Weadock et al. | 7,255,697 B2 | 8/2007 | Dycus et al. |
| 6,585,735 | B1 | 7/2003 | Frazier et al. | 7,267,677 B2 | 9/2007 | Johnson et al. |
| 6,602,252 | B2 | 8/2003 | Mollenauer | 7,270,660 B2 | 9/2007 | Ryan |
| 6,620,161 | B2 | 9/2003 | Schulze et al. | 7,270,664 B2 | 9/2007 | Johnson et al. |
| 6,620,184 | B2 * | 9/2003 | de Laforcade et al. ...... 606/205 | 7,487,780 B2 * | 2/2009 | Hooven ............... 128/898 |
| 6,626,901 | B1 | 9/2003 | Treat et al. | 2002/0013583 A1 | 1/2002 | Camran et al. |
| 6,641,595 | B1 | 11/2003 | Moran et al. | 2002/0049442 A1 | 4/2002 | Roberts et al. |
| 6,652,521 | B2 | 11/2003 | Schulze | 2002/0099372 A1 | 7/2002 | Schulze et al. |
| 6,656,177 | B2 * | 12/2003 | Truckai et al. ............... 606/51 | 2002/0107517 A1 | 8/2002 | Witt et al. |
| 6,660,072 | B2 | 12/2003 | Chatterjee | 2002/0111624 A1 | 8/2002 | Witt et al. |
| 6,669,696 | B2 | 12/2003 | Bacher et al. | 2002/0188294 A1 | 12/2002 | Couture et al. |
| 6,682,527 | B2 | 1/2004 | Strul | 2003/0014052 A1 | 1/2003 | Buysse et al. |
| 6,682,528 | B2 | 1/2004 | Frazier et al. | 2003/0014053 A1 | 1/2003 | Nguyen et al. |
| 6,685,724 | B1 | 2/2004 | Haluck | 2003/0018331 A1 * | 1/2003 | Dycus et al. ............... 606/48 |
| 6,695,840 | B2 | 2/2004 | Schulze | 2003/0018332 A1 | 1/2003 | Schmaltz et al. |
| 6,702,810 | B2 | 3/2004 | McClurken et al. | 2003/0032956 A1 | 2/2003 | Lands et al. |
| 6,726,068 | B2 | 4/2004 | Miller | 2003/0069571 A1 | 4/2003 | Treat et al. |
| 6,726,686 | B2 | 4/2004 | Buysse et al. | 2003/0078578 A1 | 4/2003 | Truckai et al. |
| 6,733,498 | B2 | 5/2004 | Paton et al. | 2003/0109875 A1 | 6/2003 | Tetzlaff et al. |
| 6,743,229 | B2 | 6/2004 | Buysse et al. | 2003/0114851 A1 | 6/2003 | Truckai et al. |
| 6,770,072 | B1 | 8/2004 | Truckai et al. | 2003/0139741 A1 | 7/2003 | Goble et al. |
| 6,773,434 | B2 | 8/2004 | Ciarrocca | 2003/0139742 A1 | 7/2003 | Wampler et al. |
| 6,776,780 | B2 | 8/2004 | Mulier et al. | 2003/0158549 A1 | 8/2003 | Swanson |
| 6,790,217 | B2 | 9/2004 | Schulze et al. | 2003/0181910 A1 | 9/2003 | Dycus et al. |
| D496,997 | S | 10/2004 | Dycus et al. | 2003/0199869 A1 | 10/2003 | Johnson et al. |
| 6,802,843 | B2 | 10/2004 | Truckai et al. | 2003/0216732 A1 | 11/2003 | Truckai et al. |
| D499,181 | S | 11/2004 | Dycus et al. | 2003/0220637 A1 | 11/2003 | Truckai et al. |
| 6,818,000 | B2 | 11/2004 | Muller et al. | 2003/0229344 A1 | 12/2003 | Dycus et al. |
| 6,860,880 | B2 | 3/2005 | Treat et al. | 2003/0236325 A1 | 12/2003 | Bonora |
| 6,887,240 | B1 | 5/2005 | Lands et al. | 2004/0030330 A1 | 2/2004 | Brassell et al. |
| 6,926,716 | B2 | 8/2005 | Baker et al. | 2004/0030332 A1 | 2/2004 | Knowlton et al. |
| 6,929,644 | B2 | 8/2005 | Truckai et al. | 2004/0049185 A1 | 3/2004 | Latterell et al. |
| 6,932,810 | B2 | 8/2005 | Ryan | 2004/0064151 A1 | 4/2004 | Mollenauer |
| 6,932,816 | B2 | 8/2005 | Phan | 2004/0082952 A1 | 4/2004 | Dycus et al. |
| 6,942,662 | B2 | 9/2005 | Goble et al. | 2004/0087943 A1 | 5/2004 | Dycus et al. |
| 6,960,210 | B2 | 11/2005 | Lands et al. | 2004/0115296 A1 | 6/2004 | Duffin |
| 6,964,662 | B2 | 11/2005 | Kidooka | 2004/0116924 A1 | 6/2004 | Dycus et al. |
| 6,994,707 | B2 | 2/2006 | Ellman et al. | 2004/0116979 A1 | 6/2004 | Truckai et al. |
| 7,011,657 | B2 | 3/2006 | Truckai et al. | 2004/0122423 A1 | 6/2004 | Dycus et al. |
| 7,033,354 | B2 | 4/2006 | Keppel | 2004/0143263 A1 | 7/2004 | Schechter et al. |
| 7,052,496 | B2 | 5/2006 | Yamauchi | 2004/0147925 A1 | 7/2004 | Buysse et al. |
| D525,361 | S | 7/2006 | Hushka | 2004/0162557 A1 | 8/2004 | Tetzlaff et al. |
| 7,083,618 | B2 | 8/2006 | Couture et al. | 2004/0176762 A1 | 9/2004 | Lawes et al. |
| 7,090,673 | B2 | 8/2006 | Dycus et al. | 2004/0193153 A1 | 9/2004 | Sarter et al. |
| 7,101,371 | B2 | 9/2006 | Dycus et al. | 2004/0225288 A1 | 11/2004 | Buysse et al. |
| 7,101,372 | B2 | 9/2006 | Dycus et al. | 2004/0230189 A1 | 11/2004 | Keppel |
| 7,101,373 | B2 | 9/2006 | Dycus et al. | 2004/0236325 A1 | 11/2004 | Tetzlaff et al. |
| 7,103,947 | B2 | 9/2006 | Sartor et al. | 2004/0243125 A1 | 12/2004 | Dycus et al. |
| 7,112,199 | B2 | 9/2006 | Cosmescu | 2004/0249371 A1 | 12/2004 | Dycus et al. |
| D531,311 | S | 10/2006 | Guerra et al. | 2004/0249374 A1 | 12/2004 | Tetzlaff et al. |
| 7,118,570 | B2 | 10/2006 | Tetzlaff et al. | 2004/0250419 A1 | 12/2004 | Sremcich et al. |
| 7,118,587 | B2 | 10/2006 | Dycus et al. | 2004/0254573 A1 | 12/2004 | Dycus et al. |
| 7,131,970 | B2 | 11/2006 | Moses et al. | 2005/0004564 A1 | 1/2005 | Wham et al. |
| 7,131,971 | B2 | 11/2006 | Dycus et al. | 2005/0004568 A1 | 1/2005 | Lawes et al. |
| 7,135,020 | B2 | 11/2006 | Lawes et al. | 2005/0004570 A1 | 1/2005 | Chapman et al. |
| D533,942 | S | 12/2006 | Kerr et al. | 2005/0021025 A1 | 1/2005 | Buysse et al. |
| 7,147,638 | B2 | 12/2006 | Chapman et al. | 2005/0021026 A1 | 1/2005 | Baily |
| 7,150,097 | B2 | 12/2006 | Sremcich et al. | 2005/0021027 A1 | 1/2005 | Shields et al. |
| 7,150,749 | B2 | 12/2006 | Dycus et al. | 2005/0033278 A1 | 2/2005 | McClurken et al. |
| D535,027 | S | 1/2007 | James et al. | 2005/0033305 A1 * | 2/2005 | Schultz ............... 606/99 |
| 7,156,846 | B2 | 1/2007 | Dycus et al. | 2005/0101951 A1 | 5/2005 | Wham et al. |
| 7,160,298 | B2 | 1/2007 | Lawes et al. | 2005/0101952 A1 | 5/2005 | Lands et al. |
| 7,160,299 | B2 | 1/2007 | Baily | 2005/0107784 A1 | 5/2005 | Moses et al. |
| 7,169,146 | B2 | 1/2007 | Truckai et al. | 2005/0107785 A1 | 5/2005 | Dycus et al. |
| 7,179,258 | B2 | 2/2007 | Buysse et al. | 2005/0113818 A1 | 5/2005 | Sartor et al. |
| 7,195,631 | B2 | 3/2007 | Dumbauld | 2005/0113819 A1 | 5/2005 | Wham et al. |
| D541,418 | S | 4/2007 | Schechter et al. | 2005/0113826 A1 | 5/2005 | Johnson et al. |

| | | | | | | |
|---|---|---|---|---|---|---|
| 2005/0113827 A1* | 5/2005 | Dumbauld et al. ............ 606/45 | EP | 0986990 | A1 | 3/2000 |
| 2005/0113828 A1 | 5/2005 | Shields et al. | EP | 1034747 | A1 | 9/2000 |
| 2005/0119655 A1 | 6/2005 | Moses et al. | EP | 1034748 | A1 | 9/2000 |
| 2005/0149151 A1 | 7/2005 | Orszulak et al. | EP | 1025807 | A3 | 10/2000 |
| 2006/0064085 A1 | 3/2006 | Schechter et al. | EP | 1034746 | A3 | 10/2000 |
| 2006/0079891 A1 | 4/2006 | Arts et al. | EP | 1050278 | A1 | 11/2000 |
| 2006/0129146 A1 | 6/2006 | Dycus et al. | EP | 1053719 | A1 | 11/2000 |
| 2006/0161150 A1 | 7/2006 | Keppel | EP | 1053720 | A1 | 11/2000 |
| 2006/0167450 A1 | 7/2006 | Johnson et al. | EP | 1055399 | A1 | 11/2000 |
| 2006/0167452 A1 | 7/2006 | Moses et al. | EP | 1055400 | A1 | 11/2000 |
| 2006/0173452 A1 | 8/2006 | Buysse et al. | EP | 1080694 | A1 | 3/2001 |
| 2006/0189980 A1 | 8/2006 | Johnson et al. | EP | 1082944 | A1 | 3/2001 |
| 2006/0189981 A1 | 8/2006 | Dycus et al. | EP | 1159926 | A2 | 12/2001 |
| 2006/0190035 A1 | 8/2006 | Hushka et al. | EP | 1301135 | A | 4/2003 |
| 2006/0217709 A1 | 9/2006 | Couture et al. | EP | 1330991 | A1 | 7/2003 |
| 2006/0224158 A1 | 10/2006 | Odom et al. | EP | 1486177 | A2 | 6/2004 |
| 2006/0259036 A1 | 11/2006 | Tetzlaf et al. | EP | 1472984 | A1 | 11/2004 |
| 2006/0264922 A1 | 11/2006 | Sartor et al. | EP | 1530952 | A1 | 5/2005 |
| 2006/0264931 A1 | 11/2006 | Chapman et al. | EP | 1532932 | A1 | 5/2005 |
| 2006/0271038 A1 | 11/2006 | Johnson et al. | EP | 1632192 | A1 | 3/2006 |
| 2007/0043352 A1 | 2/2007 | Garrison et al. | EP | 1645238 | A1 | 4/2006 |
| 2007/0043353 A1 | 2/2007 | Dycus et al. | EP | 1707143 | A1 | 10/2006 |
| 2007/0055231 A1 | 3/2007 | Dycus et al. | GB | 2214430 | A | 6/1989 |
| 2007/0062017 A1 | 3/2007 | Dycus et al. | JP | 501068 | | 9/1984 |
| 2007/0074807 A1 | 4/2007 | Guerra | JP | 502328 | | 3/1992 |
| 2007/0078456 A1 | 4/2007 | Dumbauld et al. | JP | 5-40112 | | 2/1993 |
| 2007/0078458 A1 | 4/2007 | Dumbauld et al. | JP | 06343644 | A2 | 12/1994 |
| 2007/0078459 A1 | 4/2007 | Johnson et al. | JP | 07265328 | A2 | 10/1995 |
| 2007/0088356 A1 | 4/2007 | Moses et al. | JP | 08056955 | A2 | 3/1996 |
| 2007/0106295 A1 | 5/2007 | Garrison et al. | JP | 08252263 | A2 | 10/1996 |
| 2007/0106297 A1 | 5/2007 | Dumbauld et al. | JP | 09010223 | A2 | 1/1997 |
| 2007/0118111 A1 | 5/2007 | Weinberg | JP | 11244298 | A2 | 9/1999 |
| 2007/0118115 A1 | 5/2007 | Artale et al. | JP | 2000342599 | A2 | 12/2000 |
| 2007/0142833 A1 | 6/2007 | Dycus et al. | JP | 2000350732 | A2 | 12/2000 |
| 2007/0142834 A1 | 6/2007 | Dumbauld | JP | 2001008944 | A2 | 1/2001 |
| 2007/0156139 A1 | 7/2007 | Schechter et al. | JP | 2001029356 | A2 | 2/2001 |
| 2007/0156140 A1 | 7/2007 | Baily | JP | 2001128990 | A2 | 5/2001 |
| 2007/0173811 A1 | 7/2007 | Couture et al. | SU | 401367 | | 10/1973 |
| 2007/0173814 A1 | 7/2007 | Hixson et al. | WO | WO89/00757 | | 1/1989 |
| 2007/0179499 A1 | 8/2007 | Garrison | WO | WO 92/06642 | | 4/1992 |
| 2007/0203485 A1 | 8/2007 | Keppel | WO | WO 94/08524 | A | 4/1994 |
| 2007/0213706 A1 | 9/2007 | Dumbauld et al. | WO | WO94/20025 | | 9/1994 |
| 2007/0213707 A1 | 9/2007 | Dumbauld et al. | WO | WO 95/02369 | | 1/1995 |
| 2007/0213708 A1 | 9/2007 | Dumbauld et al. | WO | WO 95/07662 | | 3/1995 |
| 2007/0213712 A1 | 9/2007 | Buysse et al. | WO | WO95/07662 | | 3/1995 |
| | | | WO | WO95/15124 | | 6/1995 |
| | FOREIGN PATENT DOCUMENTS | | WO | WO96/05776 | | 2/1996 |
| DE | 2415263 | 10/1975 | WO | WO 96/22056 | | 7/1996 |
| DE | 2627679 | 1/1977 | WO | WO 96/13218 | | 9/1996 |
| DE | 8712328 | 3/1988 | WO | WO 97/00646 | | 1/1997 |
| DE | 4303882 | 8/1994 | WO | WO 97/00647 | | 1/1997 |
| DE | 29616210 | 1/1997 | WO | WO97/10764 | | 3/1997 |
| DE | 19608716 | 4/1997 | WO | WO 97/24073 | | 7/1997 |
| DE | 19751106 | 5/1998 | WO | WO 97/24993 | | 7/1997 |
| DE | 19751108 | 5/1999 | WO | WO 98/27880 | | 7/1998 |
| EP | 0364216 A1 | 4/1990 | WO | WO 99/03407 | | 1/1999 |
| EP | 518230 A1 | 12/1992 | WO | WO 99/03408 | | 1/1999 |
| EP | 0 541 930 B1 | 5/1993 | WO | WO 99/03409 | | 1/1999 |
| EP | 0572131 | 12/1993 | WO | WO 99/12488 | | 3/1999 |
| EP | 584787 A1 | 3/1994 | WO | WO 99/40857 | | 8/1999 |
| EP | 0589453 A2 | 3/1994 | WO | WO 99/40861 | | 8/1999 |
| EP | 0623316 A1 | 11/1994 | WO | WO 99/51158 | | 10/1999 |
| EP | 0624348 A2 | 11/1994 | WO | WO 99/66850 | | 12/1999 |
| EP | 0650701 A1 | 5/1995 | WO | WO 99/66850 A | | 12/1999 |
| EP | 0694290 A3 | 3/1996 | WO | WO 00/24330 | | 5/2000 |
| EP | 0717966 A1 | 6/1996 | WO | WO00/24331 | | 5/2000 |
| EP | 0754437 A3 | 3/1997 | WO | WO 00/41638 | | 7/2000 |
| EP | 853922 A1 | 7/1998 | WO | WO00/47124 | | 8/2000 |
| EP | 0875209 A1 | 11/1998 | WO | WO 00/53112 | | 9/2000 |
| EP | 0878169 A1 | 11/1998 | WO | WO 01/17448 A | | 3/2001 |
| EP | 0887046 A3 | 1/1999 | WO | WO 01/54604 | | 8/2001 |
| EP | 0923907 A1 | 6/1999 | WO | WO02/07627 | | 1/2002 |
| | | | WO | WO 02/07627 | | 1/2002 |

| | | |
|---|---|---|
| WO | WO02/080783 | 10/2002 |
| WO | WO 02/080783 | 10/2002 |
| WO | WO02/080784 | 10/2002 |
| WO | WO 02/080784 | 10/2002 |
| WO | WO 02/080785 | 10/2002 |
| WO | WO02/080785 | 10/2002 |
| WO | WO 02/080786 | 10/2002 |
| WO | WO02/080786 | 10/2002 |
| WO | WO02/080793 | 10/2002 |
| WO | WO 02/080793 | 10/2002 |
| WO | WO02/080794 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/101311 | 12/2003 |
| WO | WO2004/032777 | 4/2004 |
| WO | WO 2004/032777 | 4/2004 |
| WO | WO 2004/052221 | 6/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO2005/004735 | 1/2005 |
| WO | WO 2005/110264 | 11/2005 |

OTHER PUBLICATIONS

Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work,Sep. 1999.
Herman et al., "Laparoscopic Intestinal Resection With the LigaSure Vessel Sealing System: A Case Report" Innovations That Work,Feb. 2002.
Carus et al., "Initial Experience With The LigaSure Vessel Sealing System in Abdominal Surgery" Innovations That Work,Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640.
Int'l Search Report PCT/US98/23950.
Int'l Search Report PCT/US99/24869.
Int'l Search Report PCT/US01/11218.
Int'l Search Report PCT/US01/11340.
Int'l Search Report PCT/US01/11420.
Int'l Search Report PCT/US02/01890.
Int'l Search Report PCT/US02/11100.
Int'l Search Report PCT/US04/03436.
Int'l Search Report PCT/US04/13273.
Int'l Search Report PCT/US04/15311.
Int'l Search Report EP 98944778.
Int'l Search Report EP 98958575.
Int'l Search Report EP 04027314.
Int'l Search Report EP 04027479.
Int'l Search Report EP 04027705.
Int'l Search Report EP 04013772.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

BILATERAL FOOT JAWS

CROSS REFERENCE TO RELATED APPLICATIONS

This application claims priority from U.S. Provisional Application Ser. No. 60/616,969 filed on Oct. 8, 2004, the contents of which are hereby incorporated by reference in their entirety.

BACKGROUND

1. Technical Field

The present disclosure relates to endoscopic surgical instruments and, more particularly, to jaws for use in connection with endoscopic instruments for grasping, sealing, dividing and/or dissecting tissue.

2. Background of Related Art

A hemostat or forceps is a simple pliers-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complimenting traditional open methods of gaining access to vital organs and body cavities with endoscopes and endoscopic instruments which access organs through small puncture-like incisions. Endoscopic instruments are inserted into the patient through a cannula, or port, that has been made with a trocar. Typical sizes for cannula range from three millimeters to twelve millimeters. Smaller cannula are usually preferred, which, as can be appreciated, ultimately presents a design challenge to instrument manufacturers who must find ways to make surgical instruments that fit through the cannula.

Certain endoscopic surgical procedures require cutting blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. However, if a larger vessel is severed, it may be necessary for the surgeon to convert the endoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, Jul. 1991, describes a bipolar coagulator which is used to seal small blood vessels. The article states that it is not possible to safely coagulate arteries with a diameter larger than 2 to 2.5 mm. A second article, entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

As mentioned above, by utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

In order to effect a proper seal with larger vessels, two predominant mechanical parameters must be accurately controlled: the pressure applied to the vessel; and the gap distance between the electrically conductive surfaces. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.005 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Various known electrosurgical instruments and methods may occasionally be able to seal larger vessels using an appropriate electrosurgical power curve, coupled with an instrument capable of applying a large closure force to the vessel walls, however, these instruments and methods rarely provide consistent and accurate vessel sealing. Moreover, the process of coagulating small vessels is fundamentally different than electrosurgical vessel sealing. For the purposes herein, "coagulation" is defined as a process of desiccating tissue wherein the tissue cells are ruptured and dried. "Vessel sealing" is defined as the process of liquefying the collagen in the tissue so that it reforms into a fused mass. Thus, coagulation of small vessels is sufficient to permanently close them. Larger vessels need to be sealed to assure permanent closure.

U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue. However, some of these designs may not provide uniformly reproducible pressure to the blood vessel and may result in an ineffective or non-uniform seal.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may prematurely move prior to activation and sealing and/or a thicker, less reliable seal may be created.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure (see, for example, commonly owned U.S. Pat. No. 6,585, 735). As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the issue during compression and prior to activation.

Typically and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Several attempts have been made to design an instrument which incorporates a knife or blade member which effectively severs the tissue after forming a tissue seal. For example, U.S. Pat. No. 5,674,220 to Fox et al. discloses a transparent vessel sealing instrument which includes a longitudinally reciprocating knife which severs the tissue once sealed. The instrument includes a plurality of openings which enable direct visualization of the tissue during the sealing and severing process. This direct visualization allows a user to visually and manually regulate the closure force and gap distance between jaw members to reduce and/or limit certain undesirable visual effects known to occur when sealing vessels, thermal spread, charring, etc. As can be appreciated, the overall success of creating an effective tissue seal with this instrument is greatly reliant upon the user's expertise, vision, dexterity, and experience in judging the appropriate closure force, gap distance and length of reciprocation of the knife to uniformly, consistently and effectively seal the vessel and separate the tissue at the seal along an ideal cutting plane.

U.S. Pat. No. 5,702,390 to Austin et al. discloses a vessel sealing instrument which includes a triangularly-shaped electrode which is rotatable from a first position to seal tissue to a second position to cut tissue. Again, the user must rely on direct visualization and expertise to control the various effects of sealing and cutting tissue.

Thus, a need exists to develop an electrosurgical instrument which effectively and consistently seals and separates vascular tissue and solves many of the aforementioned problems known in the art.

SUMMARY

The present disclosure relates to a surgical instrument which comprises a drive rod assembly including an elongated hollow shaft portion having a proximal and a distal end and a central shaft slidably disposed in and axially aligned with the hollow shaft portion. The instrument may further include a handle assembly coupled to the hollow shaft portion and the central shaft of the drive rod assembly, the handle assembly configured to actuate the drive rod assembly. A pair of opposing jaw members may be included each operatively associated with the distal end of the hollow shaft portion, the jaw members being movable relative to one another between a first position wherein the jaw members are disposed in spaced relation relative to one another and a second position wherein the jaw members are approximated towards one another. The instrument may further include a source of electrical energy connected to each jaw member for conducting energy therebetween.

In one embodiment of the present disclosure the surgical instrument may include an activator included in the handle assembly, the activator having a movable handle and a fixed handle which cooperate to lock and unlock the jaw members. Moreover, the instrument may further include a rotating assembly attached to the handle assembly, the rotating assembly configured to control rotation of the end effector assembly.

In another embodiment of the present disclosure each jaw member may include a jaw housing defining a tissue contacting surface, the jaw housing includes a flange extending proximally therefrom and a cam arm extending from the flange. It is envisioned that the jaw members may be configured to pivot as the elongated hollow shaft portion is axially displaced relative to the central shaft. In one embodiment the jaw members are configured to pivot about a pivot pin.

In yet another embodiment of the present disclosure the central shaft further includes a bifurcated distal end defining a pair of arms and a cavity between the arms for receiving the flanges of jaw members.

It is envisioned that there may be electrically conductive sealing surfaces disposed on each jaw member, the electrically conductive sealing surfaces being electrically connected to the source of electrical energy. Moreover, each jaw member may be electrically isolated from one another.

In certain embodiments of the present disclosure the surgical instrument may further include a knife assembly for separating tissue, the knife assembly slidably supported in the elongate hollow shaft being configured and dimensioned to cut tissue grasped between jaw members.

It is envisioned that a wide variety of materials may be utilized in constructing the electrosurgical instrument of the present disclosure. For example, the cam arms may be constructed of a resilient material or the jaw members may be wholly or partially constructed of titanium or stainless steel. Moreover, the sealing surfaces may be coated with, inter alia, a non-stick material.

In one embodiment of the present disclosure the cam arm of a first jaw member may extend through a first aperture formed in the hollow shaft portion and the cam arm of a second jaw member to extend through a second aperture formed in the hollow shaft portion. The proximal displacement of the hollow shaft portion relative to the central shaft results in a distal surface of said apertures engaging a distal surface of said cam arms to move the jaw members to the second position. The distal displacement of the hollow shaft portion relative to the central shaft results in a proximal surface of said apertures engaging a proximal surface of said cam arms to move the jaw members to the first position.

In another embodiment of the present disclosure at least one of the pair of jaw members is partially constructed of a hard anodized aluminum having a high dielectric strength which electrically isolates the jaw members and confines the electrosurgical energy between the electrically conductive sealing surfaces.

In another embodiment a switching mechanism for selecting between a variety of heating technologies is provided. Some possible switches could include hand switches, foot switches, wafer switches, etc.

In yet another embodiment of the present disclosure a surgical instrument is disclosed, the instrument comprising a drive rod assembly including an elongated hollow shaft portion having a proximal and a distal end and a central shaft slidably disposed in and axially aligned with the hollow shaft portion. The instrument may further include a handle assembly coupled to the hollow shaft portion and the central shaft of the drive rod assembly, the handle assembly configured to actuate the drive rod assembly. A pair of opposing jaw members may be included each operatively associated with the distal end of the hollow shaft portion, the jaw members being movable relative to one another between a first position wherein the jaw members are disposed in spaced relation relative to one another and a second position wherein the jaw members are approximated towards one another. Each jaw member includes a cam arm, each cam arm extending from a proximal end, the cam arms being configured and dimensioned to pivot the jaw members between open and closed positions when the elongated hollow shaft portion is axially displaced relative to the central shaft. A source of electrical energy connected to each jaw member may also be provided for conducting energy therebetween.

In one embodiment of the present disclosure the instrument may further include electrically conductive sealing surfaces having a series of stop members, the stop members configured to facilitate gripping and manipulation of tissue and defining a gap between the jaw members.

In another embodiment, the cam arm of a first jaw member extends through a first aperture formed in the hollow shaft portion and the cam arm of a second jaw member extends through a second aperture formed in the hollow shaft portion. Proximal displacement of the hollow shaft portion relative to the central shaft results in a distal surface of said apertures engaging a distal surface of said cam arms to move the jaw members to the second position. Distal displacement of the hollow shaft portion relative to the central shaft results in a proximal surface of said apertures engaging a proximal surface of said cam arms to move the jaw members to the first position.

BRIEF DESCRIPTION OF THE DRAWINGS

By way of example only, embodiments of the endoscopic instrument of the present disclosure will be described with reference to the accompanying drawings, in which.

DETAILED DESCRIPTION

Detailed embodiments of the presently disclosed instruments, devices and systems will now be described in detail with reference to the drawing figures wherein like reference numerals identify similar or identical elements. In the drawings and in the description which follows, the term "proximal", as is traditional, will refer to the end of the instrument, device and/or system which is closest to the operator while the term "distal" will refer to the end of the instrument, device and/or system which is furthest from the operator.

Figure 1:
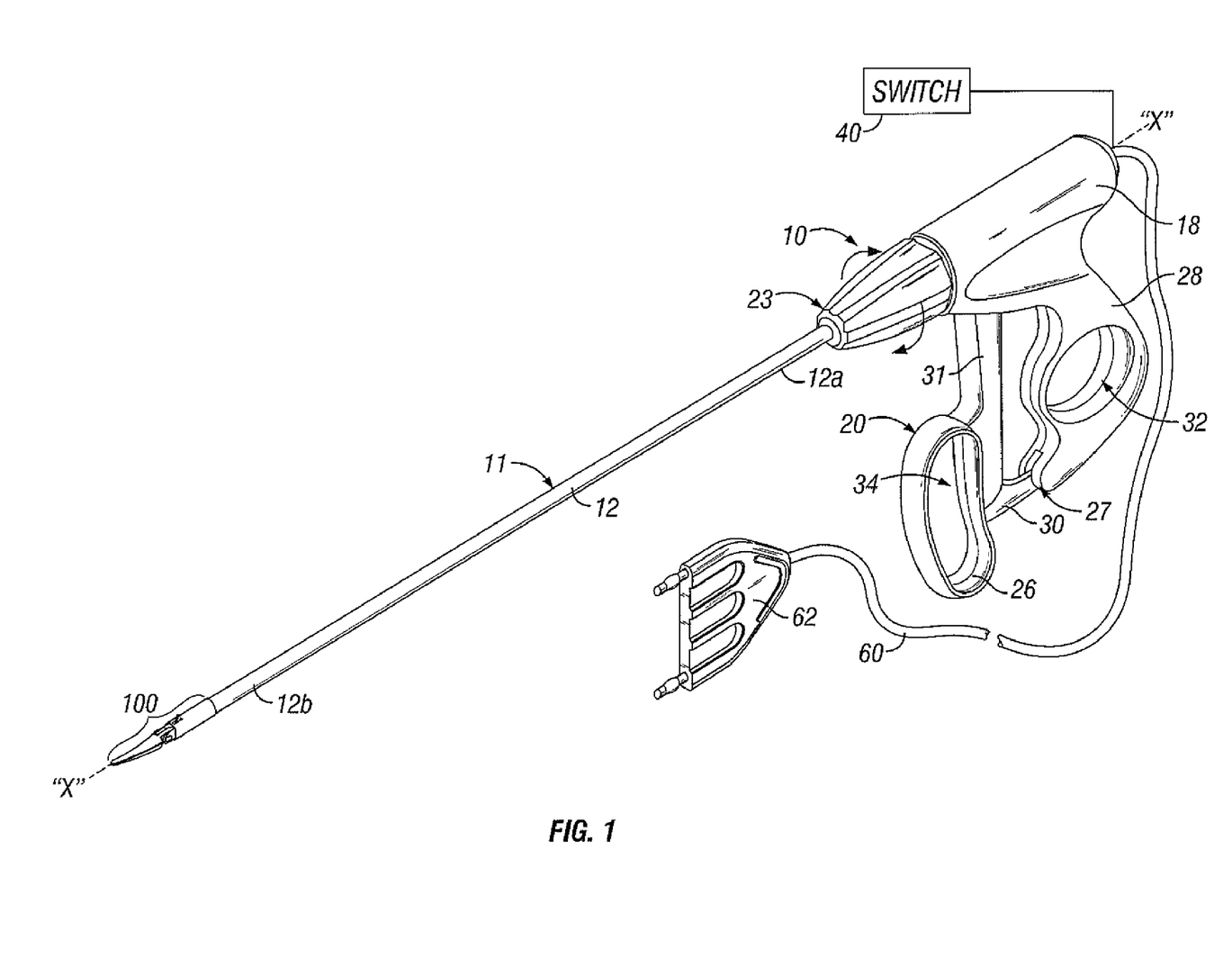
FIG. 1 is a perspective view of an endoscopic instrument according to one embodiment of the present disclosure.
Figure 2:
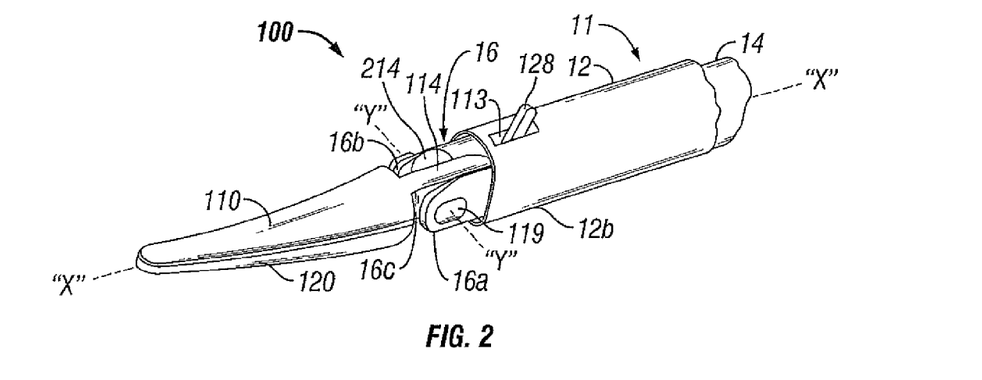
FIG. 2 is an enlarged, perspective view of an end effector assembly of the endoscopic instrument of FIG. 1.

Referring to FIGS. 1 and 2, an endoscopic instrument according to an embodiment of the present disclosure is designated generally as reference numeral 10. Endoscopic instrument 10 includes a drive rod assembly 11 which is coupled to a handle assembly 18. Drive rod assembly 11 includes an elongated hollow shaft portion 12 having a proximal end 12a and a distal end 12b. Drive rod assembly 11 further includes a central shaft 14 slidably disposed in and axially aligned with hollow shaft portion 12. Central shaft 14 includes a bifurcated distal end 16 including arms 16a, 16b which, together, define a cavity 16c for receiving flanges 114, 124 of jaw members 110, 124, as will be described in greater detail below.

An end effector assembly 100 is attached to distal end 16 of central shaft 14 and includes a pair of opposing jaw members 110 and 120 which are operatively associated with distal end 12b of hollow shaft portion 12. Preferably, handle assembly 18 is attached to proximal end 12a of hollow shaft portion 12 and includes an activator 20 for imparting movement of jaw members 110 and 120 from an open position wherein jaw members 110 and 120 are disposed in spaced relation relative to one another, to a clamping or closed position wherein jaw members 110 and 120 cooperate to grasp tissue therebetween.

With continued reference to FIGS. 1 and 2, activator 20 includes a movable handle 26 having an aperture 34 defined therein for receiving at least one of the operator's fingers and a fixed handle 28 having an aperture 32 defined therein for receiving an operator's thumb. Movable handle 26 is selectively movable from a first position relative to fixed handle 28 to a second position in closer proximity to fixed handle 28 to close jaw members 110 and 120. Preferably, fixed handle 28 includes a channel 27 which extends proximally for receiving a ratchet 30 which is coupled to movable handle 26. Ratchet 30 is preferably designed to allow a user to progressively lock, at multiple positions, and subsequently release movable handle 26 relative to fixed handle 28. The handle structure, in turn, allows for progressive closure of end effector assembly 100 as well as locking engagement of opposing jaw members 110, 120. In some cases it may be preferable to include other mechanisms to control and/or limit the movement of handle 26 relative handle 28, such as, for example, hydraulic, semi-hydraulic and/or gearing systems.

Desirably, fixed handle 28 includes a rotating assembly 23 for controlling the rotational movement of end effector assembly 100 about a longitudinal axis "X" of elongated hollow shaft portion 12. In use, as rotating assembly 23 is rotated about the longitudinal "X" axis, end effector assembly 100 is also rotated about the longitudinal "X" axis.

Figure 3:
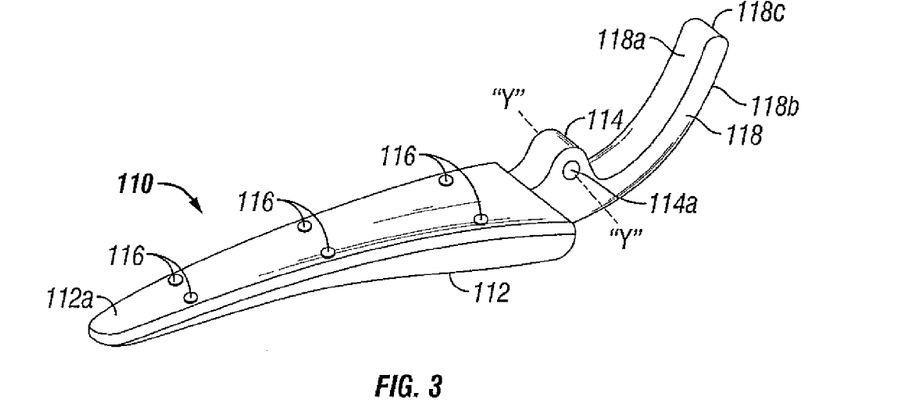
FIG. 3 is a perspective view of a jaw member of the endoscopic instrument of FIG. 1.
Figure 4:
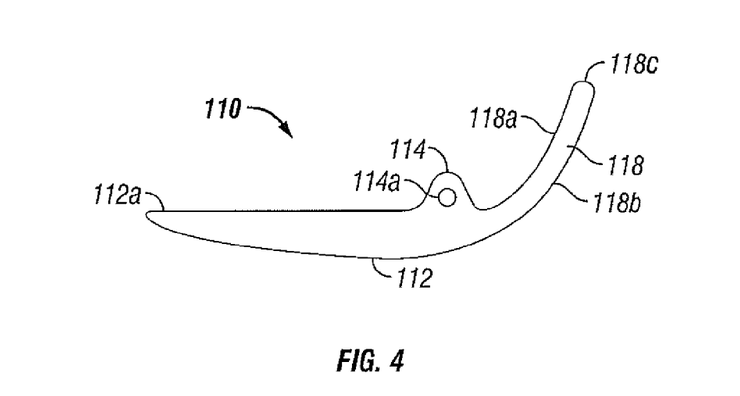
FIG. 4 is a side, elevational view of a jaw member of FIG. 3.

With reference to FIGS. 2-4, end effector assembly 100 includes a first jaw member 110 and a second jaw member 120, pivotably connected between arms 16a, 16b of distal end 16 of central shaft 14. Preferably, jaw members 110, 120 are movable from an open position to a closed position by movement of handle assembly 18 as described above. Jaw members 110, 120 are generally symmetrical and include similar component features which cooperate to permit facile rotation about pivot pin 119 to effect opening and closing of end effector assembly 100. As a result, and unless otherwise noted, only jaw member 110 and the operative features associated therewith are described in detail herein but as can be appreciated, many of these features apply to jaw member 120 as well.

First jaw member 110 includes a jaw housing 112 having a flange 114 extending proximally therefrom. Flange 114 includes a pivot hole 114a formed therethrough for receiving pivot pin 119 (see FIG. 2). Jaw housing 112 of first jaw member 110 defines a tissue contacting surface 112a which is juxtaposed with respect to a tissue contacting surface 122a of second jaw member 120 (see FIGS. 5-7).

First jaw member 110 further includes a cam arm 118 extending from flange 114. Preferably, cam arm 118 is arcuate and extends in a direction proximally from flange 114 and across a plane defined by tissue contacting surface 112a. Cam arm 118 includes a distal camming surface 118a, a proximal camming surface 118b, and terminates in a proximal tip 118c. Proximal tip 118c of cam arm 118 is preferably located beyond a plane which extends through central axis "Y" of pivot hole 114a and which is parallel to the plane defined by tissue contacting surface 112a.

As seen in FIGS. 2 and 5-7, proximal tips 118c, 128c of cam arms 118, 128 of first and second jaw members 110, 120 extend through apertures or slots 113, 123 formed at or near distal end 12b of hollow shaft 12. In particular, proximal tip 118c of first jaw member 110 extends through aperture 113, and proximal tip 128c of second jaw member 120 extends through aperture 123. Desirably, apertures 113, 123 are substantially diametrically opposed from one another.

Each aperture 113, 123 includes a distal surface 113a, 123a, respectively, which engages respective distal camming surfaces 128a, 118a of cam arms 128, 118. Each aperture 113, 123 further includes a proximal surface 113b, 123b, respectively, which engages respective proximal camming surfaces 128b, 118b of cam arms 128, 118.

As will be described in greater detail below, as hollow tubular shaft 12 is axially displaced relative to central shaft 14, proximal or distal surfaces of apertures 113, 123 engage distal 118a, 128a or proximal 118b, 128b camming surfaces of cam arms 118, 128 to thereby pivot jaw members 110, 120 about pivot pin 119, between open and closed positions.

Desirably, each cam arm 118, 128 is fabricated from a material having a degree of flexibility and resiliency that enables cam arms 118, 128 to act as leaf springs. As will be described in greater detail below, when hollow shaft portion 12 is displaced sufficiently proximal, relative to central shaft 14 and end effector 100, cam arms 118, 128 will flex and be cammed into hollow shaft portion 12.

Figure 5:
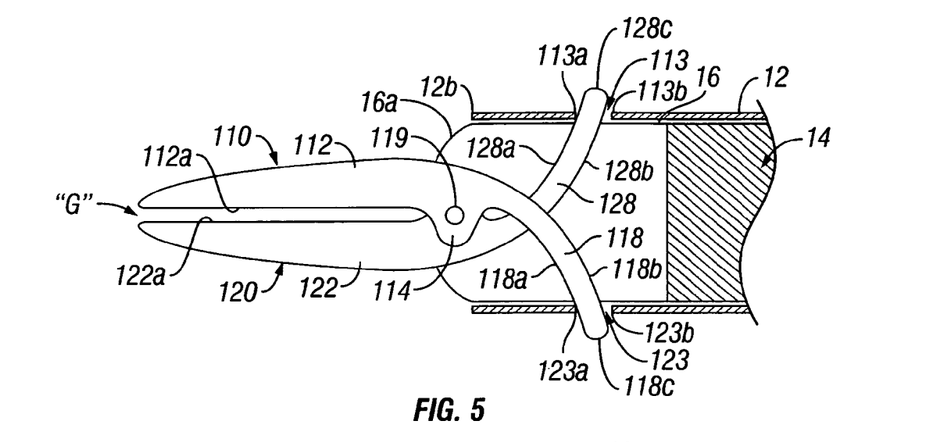
FIG. 5 is a schematically illustrated side elevational view of the end effector assembly of FIG. 2, illustrating the end effector assembly in a closed condition.
Figure 6:
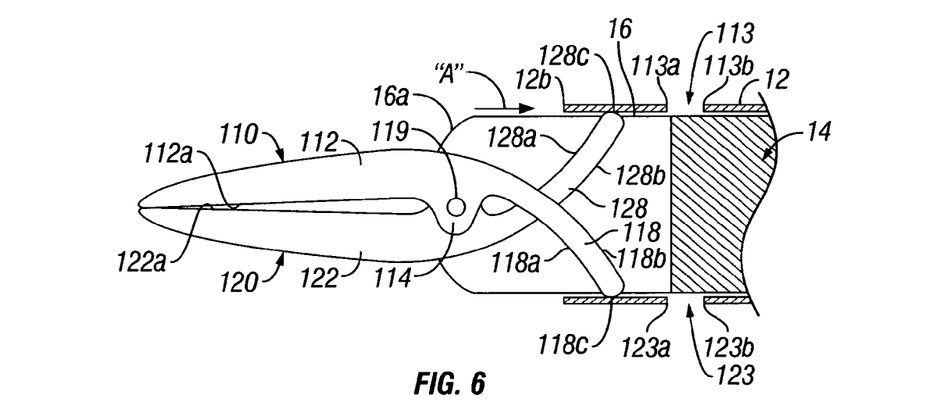
FIG. 6 is a schematically illustrated side elevational view of the end effector assembly of FIG. 2, illustrating the end effector assembly in a clamped condition.
Figure 7:
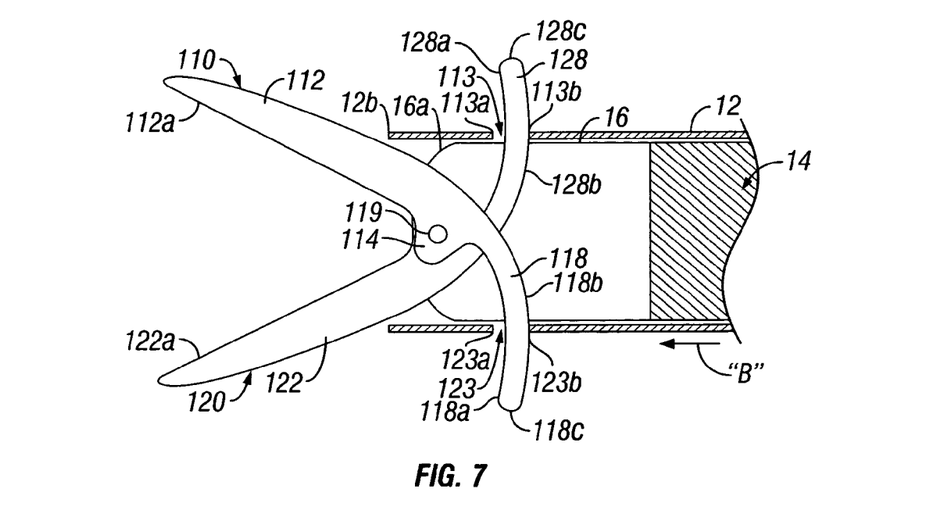
FIG. 7 is a schematically illustrated side elevational view of the end effector assembly of FIG. 2, illustrating the end effector assembly in an open condition.

Turning now to FIGS. 5-7, operation and use of endoscopic instrument 10, including end effector 100, is shown and described. Referring initially to FIG. 5, instrument 10 and end effector 100 are in a first position in which end effector is in a closed condition. As seen in FIG. 5, with end effector 100 closed, cam arm 118 of first jaw member 110 extends through aperture 123 formed in hollow shaft portion 12, and cam arm 128 of second jaw member 120 extends through aperture 113 formed in hollow shaft portion 12.

Desirably, when in the closed position, end effector 100 defines a gap distance "G" between tissue contact surface 112a of first jaw member 110 and tissue contact surface 122a of second jaw member 120. Preferably, gap distance "G", between opposing tissue contact surfaces 112a, 122a, ranges from about 0.001 inches to about 0.006 inches and, more preferably, between about 0.002 inches and about 0.003 inches.

Alternatively, one or a series of stop members 116 (shown in FIG. 3) may be employed on the inner facing surfaces of the electrically conductive sealing surfaces to facilitate gripping and manipulation of tissue and to define the gap "G" between the opposing jaw members. A detailed discussion of these and other envisioned stop members as well as various manufacturing and assembling processes for attaching and/or affixing the stop members to the electrically conductive sealing surfaces are described in commonly assigned, co-pending U.S. Pat. No. 7,473,253 entitled "Vessel Sealer and Divider with Non-Conductive Stop Members" by Dycus et al., which is hereby incorporated by reference in its entirety herein.

End effector 100 is manipulatable to a second position, as seen in FIG. 6, in which end effector 100 is in a clamped condition. In doing so, first and second jaw members 110, 120 are pivoted about pivot pin 119 to move the distal-most ends of first and second jaw members 110, 120 toward one another and pinch or clamp tissue disposed therebetween. End effector 100 is manipulated from the first position to the second position by axially displacing hollow shaft portion 12 in a proximal direction relative to central shaft 14 and end effector 100, as indicated by arrow "A" in FIG. 6, and/or by axially displacing central shaft 14 and end effector 100 in a distal direction relative to hollow shaft portion 12.

By moving hollow shaft portion 12 in a proximal direction, e.g., in the direction of arrow "A", relative to central shaft 16, distal surfaces 113a, 123a of apertures 113, 123 engage distal camming surfaces 128a, 118a, respectively of cam arms 128 and 118. As hollow shaft portion 12 is moved in the direction of arrow "A", distal surfaces 113a, 123a cam against distal camming surfaces 128a, 118a, respectively, thereby moving cam arms 118, 128 towards one another and pivoting jaw members 110, 120 about pivot pin 119 to move the distal-most tips thereof towards one another.

Since cam arms 118, 128 are flexible and resilient, continued movement of hollow shaft portion 12, in the direction of arrow "A", results in cam arms 118, 128 deflecting and/or biasing toward one another until proximal tips 118c, 128c are desirably disposed within or drawn into hollow shaft portion 12. Preferably, jaw members 110, 120 are pivoted about pivot pin 119 by an amount sufficient for the distal-most tips thereof to contact one another and pinch or clamp any tissue disposed therebetween.

Deflection and/or biasing of cam arms 118, 128 towards one another creates a clamping force or load on or along tissue contact surfaces 112a, 122a. No other biasing members are needed to achieve the clamping force along tissue contact surfaces 112a, 122a. Alternatively, jaw members 110 and 120 and cam arms 118 and 128 may be dimensioned to enable a surgeon to seal tissue. For example, the user may initially move shaft portion 12 proximally to engage distal surfaces 113a and 123a to close jaw members 110 and 120 to allow the user to manipulate tissue (i.e., the tips of jaw members 110 and 120 may orient relative to one another to allow accurate manipulation and dissection similar to FIG. 6). Upon further movement of shaft portion 12, cam arms 118 and 128 may be urged through apertures 113 and 123 to close jaw members 110 and 120 about tissue to promote tissue sealing. Preferably, jaw members 110 and 120 and cam arms 118 and 128 will maintain a closure force within about 3 kg/cm$^2$ to about 16 kg/cm$^2$. Desirably, one or more stop members may be provided for maintaining gap distance "G", between opposing tissue contact surfaces 112a, 122a, in a range from about 0.001 inches to about 0.006 inches and, more preferably, between about 0.002 inches and about 0.003 inches.

End effector 100 is manipulatable to a third position, as seen in FIG. 7, in which end effector 100 is in an open condition. In doing so, first and second jaw members 110, 120 are pivoted about pivot pin 119 to move the distal-most ends of first and second jaw members 110, 120 away from one another. End effector 100 is manipulated from the first or second position to the third position by axially displacing hollow shaft portion 12 in a distal direction relative to central shaft 14 and end effector 100, as indicated by arrow "B" in FIG. 7, and/or by axially displacing central shaft 14 and end effector 100 in a proximal direction relative to hollow shaft portion 12.

By moving hollow shaft portion 12 in a distal direction, e.g., in the direction of arrow "B", relative to central shaft 14, proximal surfaces 113b, 123b of apertures 113, 123 engage proximal camming surfaces 128b, 118b, respectively of cam arms 128 and 118. As hollow shaft portion 12 is moved in the direction of arrow "B", proximal surfaces 113b, 123b cam against proximal camming surfaces 128b, 118b, respectively, thereby moving cam arms 118, 128 away from one another and pivoting jaw members 110, 120 about pivot pin 119 to separate the distal-most tips thereof away from one another.

Moving end effector 100 to the open condition allows for easier insertion of tissue between first and second jaw members 110, 120. Additionally, by continually moving end effector 100 to the open condition, first and second jaw members 110, 120 may act as dissectors for separating tissue and the like.

As seen in FIG. 7, distal displacement of hollow shaft portion 12 is preferably limited such that a distal-most edge thereof does not contact either of first or second jaw members 110, 120 and thereby interfere with the opening of end effector 100. Desirably, the distance between the distal-most edge of hollow shaft portion 12 and the distal surfaces 113a, 123a of apertures 113, 123 is minimized in order to reduce the possibility and/or likelihood of the distal-most edge of hollow shaft portion 12 contacting first or second jaw member 110, 120.

Figure 8:
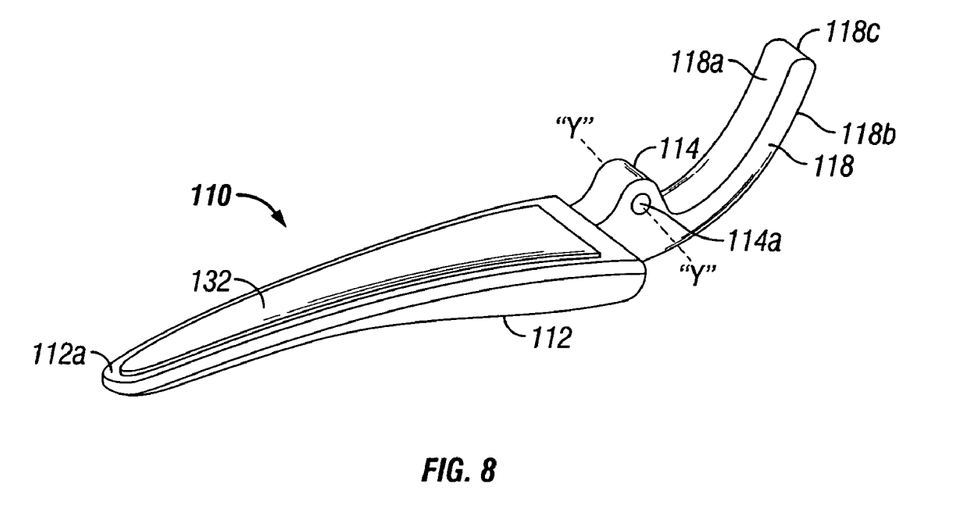
FIG. 8 is a perspective view of a jaw member according to an alternate embodiment of the present disclosure.
Figure 9:
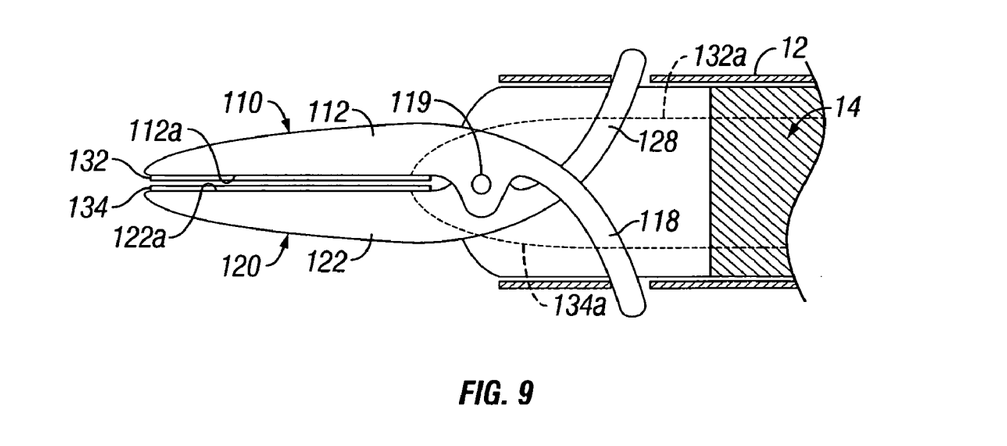
FIG. 9 is a schematically illustrated side elevational view of an end effector assembly including the jaw members of FIG. 8, illustrating the end effector assembly in a closed condition.

Turning now to FIGS. 8 and 9, it is contemplated and within the scope of the present disclosure, for each jaw member 110, 120 to include an electrically conductive sealing surface or face plate 132, 134, respectively, disposed on tissue contact surfaces 112a, 122a thereof. Sealing surfaces 132, 134 may be joined to respective jaw housings 112, 122 by pinning, welding, gluing, bolting or any other sufficiently rigid and/or secure method.

It is envisioned that jaw housings 112, 122 may be fabricated from any material which is suitable for its intended purpose, such as, for example, stainless steel, titanium, or the like. It is further envisioned that jaw housings 112, 122 may be manufactured from non-conductive materials, such as ceramics and the like. In this embodiment, electrically conductive sealing surfaces 132, 134 may be coated onto the ceramic-like material of jaw housings 112, 122.

Electrically conductive sealing surfaces 132, 134 are each electrically connected to respective cable leads 132a, 134a, through which electrosurgical energy is transmitted to sealing surfaces 132, 134. Desirably, cable leads 132a, 134a are isolated from one another.

Alternatively, it is envisioned that each jaw member 110, 120 may be fabricated from an electrically conductive material and electrically connected to a respective lead. In this embodiment, jaw members 110, 120 are preferably electrically isolated from one another by a bushing or washer (not shown) placed at the pivot between respective flanges 114, 124.

Figure 10:
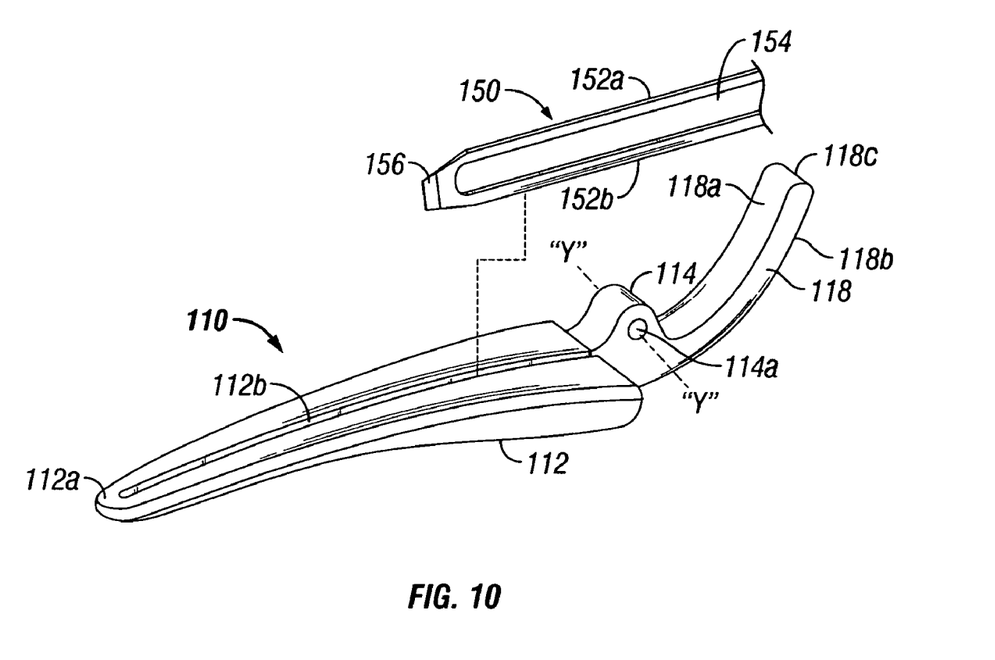
FIG. 10 is an exploded perspective view of a jaw member according to an alternate embodiment of the present disclosure, illustrating an elongated knife operatively associated therewith.
Figure 11:
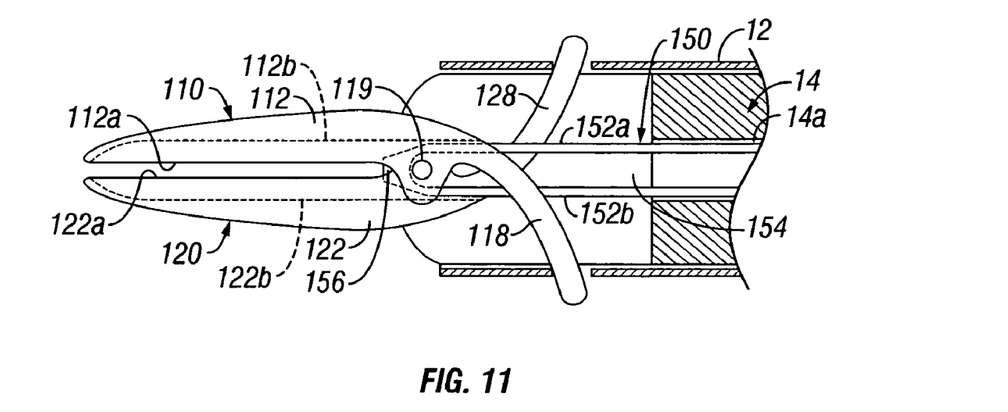
FIG. 11 is a schematically illustrated view of a jaw member according to the FIG. 10 embodiment illustrating the operative association of the knife therewith.

Turning now to FIGS. 10 and 11, it is contemplated and within the scope of the present disclosure for endoscopic instrument 10 to be configured and adapted to include a knife 150 operatively associated therewith. In particular, as seen in FIG. 10, each jaw member 110, 120 includes a knife slot 112b, 122b formed therein for slidably receiving a distal end of knife 150. In addition, central shaft 14 includes a lumen 14a formed therethrough for slidably receiving a proximal end of knife 150.

Knife 150 includes a pair of spaced apart forks 152a, 152b defining a slot 154 therebetween, and a knife blade 156 formed or provided at a distal end thereof. In this manner, knife 150 is operatively connected to endoscopic instrument 10 such that pivot pin 119 is slidably disposed within slot 154. Accordingly, as knife 150 is reciprocated through knife slots 112b, 122b of jaw members 110, 120, respectively, pivot pin 119 translates through slot 154 of knife 150.

In one embodiment, it is contemplated that knife 150 can translate through knife slots 112a, 122a to cut the tissue grasped between jaw members 110 and 120 only while jaws members 110 and 120 are closed. In particular, knife 150 may only be advanced through the tissue when jaw members 110 and 120 are closed thus preventing accidental or premature activation or advancement of knife 150 through the tissue. Put simply, at least one of knife slots 112a, 122a is blocked when jaws members 110 and 120 are opened and aligned for activation when jaw members 110 and 120 are closed. U.S. patent application Ser. No. 10/873,860 discloses and describes various lock-out mechanism which may be utilized for this purpose.

While jaw members 110, 120 are shown as being substantially linear, including substantially linear knife slots 112b, 122b formed therein, it is envisioned that jaw members 110, 120 may be arcuate and include arcuate knife slots 112b, 122b formed therein. As such, knife 150 may be made from a semi-compliant material or may be multi-segmented to assure consistent, facile and accurate cutting and/or reciprocation through knife slots 112b, 122b.

From the foregoing and with reference to the various figure drawings, those skilled in the art will appreciate that certain modifications can also be made to the present disclosure without departing from the scope of the same.

Experimental results suggest that the magnitude of pressure exerted on the tissue by jaw members 110, 120 is important in assuring a proper surgical outcome. Tissue pressure within a working range of about 3 kg/cm$^2$ to about 16 kg/cm$^2$ and, preferably, within a working range of 7 kg/cm$^2$ to 13 kg/cm$^2$ have been shown to be effective for sealing arteries and vascular bundles.

It is envisioned that the outer surface of the end effector may include a nickel-based material, coating, stamping, metal injection molding which is designed to reduce adhesion between the end effector (or components thereof) with the surrounding tissue during operation thereof. Moreover, it is also contemplated that the tissue contacting surfaces 112 and 122 and, more particularly, sealing surfaces 132, 134 of jaw members 110, 120 may be manufactured from one (or a combination of one or more) of the following materials: nickel-chrome, chromium nitride, MedCoat 2000 manufactured by The Electrolizing Corporation of OHIO, inconel 600 and tin-nickel. Sealing surfaces 132, 134 may also be coated with one or more of the above materials to achieve the same result, i.e., a "non-stick surface". Preferably, the non-stick materials are of a class of materials that provide a smooth surface to prevent mechanical tooth adhesions. As can be appreciated, reducing the amount that the tissue "sticks" during sealing improves the overall efficacy of the instrument. Reference may be made to commonly assigned and owned U.S. patent application Ser. No. 10/284,562 entitled "Vessel Sealing Instrument", which is hereby incorporated by reference in its entirety herein, for a detailed discussion of the manufacture of the sealing surfaces.

When utilized on sealing surfaces 132, 134, these materials provide an optimal surface energy for eliminating sticking due in part to surface texture and susceptibility to surface breakdown due electrical effects and corrosion in the presence of biologic tissues. It is envisioned that these materials exhibit superior non-stick qualities over stainless steel and should be utilized on instrument 10 in areas where the exposure to pressure and electrosurgical energy can create localized "hot spots" more susceptible to tissue adhesion.

As mentioned above, the non-stick materials may be manufactured from one (or a combination of one or more) of the following "non-stick" materials: nickel-chrome, chromium nitride, MedCoat 2000, Inconel 600 and tin-nickel. For example, high nickel chrome alloys, Ni200, Ni201 (~100% Ni) may be made into electrodes or sealing surfaces by metal injection molding, stamping, machining or any like process. Also and as mentioned above, sealing surfaces 132, 134 may also be "coated" with one or more of the above materials to achieve the same result, i.e., a "non-stick surface". For example, Nitride coatings (or one or more of the other above-identified materials) may be deposited as a coating on another base material (metal or nonmetal) using a vapor deposition manufacturing technique.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

By way of example, chromium nitride may be applied using a physical vapor deposition (PVD) process that applies a thin uniform coating to the entire electrode surface. This coating produces several effects: 1) the coating fills in the microstructures on the metal surface that contribute to mechanical adhesion of tissue to electrodes; 2) the coating is very hard and is a non-reactive material which minimizes oxidation and corrosion; and 3) the coating tends to be more resistive than the base material causing electrode surface heating which further enhances desiccation and seal quality.

The Inconel 600 coating is a so-called "super alloy" which is manufactured by Special Metals, Inc. located in Conroe Tex. The alloy is primarily used in environments which require resistance to corrosion and heat. The high Nickel content of Inconel makes the material especially resistant to organic corrosion. As can be appreciated, these properties are desirable for bipolar electrosurgical instruments which are naturally exposed to high temperatures, high RF energy and organic matter. Moreover, the resistivity of Inconel is typically higher than the base electrode material which further enhances desiccation and seal quality.

Another embodiment of the present disclosure includes jaw members 110, 120 fabricated from a hard anodized aluminum with or without the use of a synthetic sealed coating made from a resinous fluorine containing polymers or polytetrafluoroethylene, commonly sold under the trademark Teflon™, on electrically non-conductive components of one or both of jaw members 110 and 120 (i.e., the areas surrounding the conductive surfaces) to control the electrical path between jaw members 110 and 120 during electrosurgical activation and to reduce sticking. Other materials which tend to reduce tissue adherence include: nickel-chrome, chromium nitride, Ni200, Ni201, Inconel 600, tin-nickel. It is envisioned that utilizing a hard anodized aluminum on the non-sticking surface of at least one of jaw members 110 and 120 electrically isolates jaw members 110 and 120 from one another and confines the electrosurgical energy between the conductive sealing surfaces. The non-stick coating reduces undesirable sticking of the tissue to components of jaw members 110, 120 during the sealing process.

Preferably, the hard anodized aluminum has a high dielectric strength and good wear properties and has a thickness of about 0.001 to about 0.003 inches. It has been found that electrically insulating the aluminum jaw members 110 and 120 from other surrounding components confines the electrical path to between jaw members 110 and 120 and eliminates alternate current paths which can result in collateral tissue damage.

It is also contemplated that the presently disclosed embodiments herein may be designed to seal the tissue structure using so-called "resistive heating" whereby sealing surfaces 132 and 134 are not necessarily electrically conductive surfaces. Rather, each of sealing surfaces 132 and 134 is heated much like a conventional "hot plate" such that sealing surfaces 132 and 134 cooperate to seal the tissue upon contact (or upon activation of a switch (not shown) which selectively heats each sealing surfaces 132 and 134 upon activation). "Resistive heating" is achieved by controlling the temperature between a range of about 125 to about 150 degrees Celsius, controlling the pressure between a range of about 100 psi to about 200 psi, and regulating the gap distance.

It is also envisioned that the tissue may be sealed and/or fused using radio frequency (RF) energy. With this embodiment, the electrodes which transmit the RF energy may be configured as a large solid blocks or a multiple smaller blocks separated by an insulator. More particularly, the surgeon can selectively regulate the transmission of RF energy to a pair of thermally isolated jaw members 110 and 120 which, in turn, transmits the RF energy through the tissue which acts as a resistive medium. By regulating the RF energy, the temperature of the tissue is easily controlled. The closing pressure between jaw members 110 and 120 may be selectively regulated by adjusting the configuration of cam arms 118, 128.

Preferably, the closing pressure is in the range of about 100 to about 200 psi. It has been determined that by controlling the RF energy and pressure and maintaining a gap distance "G" in the range of about 0.003 millimeters to about 0.015 millimeters between sealing surfaces 132 and 134, effective and consistent tissue sealing may be achieved in a broad range of tissue types.

Alternatively, instrument 10 may employ any combination of one or more of the above heating technologies and a switch 40 (shown in FIG. 1) which allows the surgeon the option of select between the different heating technologies.

Although any of the instruments described herein may be designed to seal and divide tissue through standard-sized cannula, one envisioned embodiment of the present disclosure includes a reduced-diameter shaft 12 and end effector assembly 100 which is specifically dimensioned to fit through a 5 mm cannula. As can be appreciated, utilizing a smaller-sized surgical instrument can be extremely beneficial to the patient (i.e., reduced trauma, healing and scar tissue).

Preferably, any of the instruments disclosed herein may be designed to be electrically couple to a foot switch (not shown) which allows the surgeon to selectively control the electrosurgical energy transferred to the tissue. In an alternate embodiment, instrument 10 may be activated via a handswitch (not shown) located on the trigger assembly. More particularly, the handswitch includes a pair of wafer switches (not shown) which are disposed on either side of the trigger. The wafer switches cooperate with an electrical connector (not shown) disposed within housing 20. It is envisioned that the wafer switches are mounted in such a manner that upon activation of the trigger assembly the wafer switches are intentionally moved out of electrical contact with the connector. As can be appreciated, this prevents accidental activation of the jaw members 110 and 120 during cutting. Alternatively, other safety measures may also be employed, e.g., a cover plate which insulates the switches from the connector upon actuation of the trigger assembly, a cut-off switch, etc. Reference may be made to commonly assigned and owned U.S. patent application Ser. No. 10/460,926, which is hereby incorporated by reference in its entirety herein, for a detailed discussion of other safety measures which may be employed.

As mentioned above, it is also envisioned that knife 150 may be energized. It is envisioned that the wafer switches could be reconfigured such that in one position, the wafer switches activate jaw members 110 and 120 upon actuation and in another position, the wafer switches activate knife 150. Alternatively, the wafer switches may be designed as mentioned upon (i.e., with a single electrical connector) which energizes both knife 150 and jaw members 110 and 120 simultaneously. In this case, knife 150 may need to be insulated to prevent shorting.

As can be appreciated, locating handswitch on instrument 10 has many advantages. For example, the handswitch reduces the amount of electrical cable in the operating room and eliminates the possibility of activating the wrong instrument during a surgical procedure due to "line-of-sight" activation. Moreover, decommissioning the handswitch when the trigger is actuated eliminates unintentionally activating the device during the cutting process.

It is also envisioned that the handswitch may be disposed on another part of instrument 10, e.g., the handle assembly 30, rotating assembly, housing 20, etc. In addition, although wafer switches are shown in the drawings, other types of switches employed which allow the surgeon to selectively control the amount of electrosurgical energy to jaw members 110, 120 or knife 150, e.g., toggle switches, rocker switches, flip switches, etc.

It is also contemplated that in lieu of a knife 150, the present disclosure may include a so-called "hot-wire" (not shown) inter-disposed between the two jaw members 110 and 120 which is selectively activateable by the user to divide the tissue after sealing. More particularly, a separate wire is mounted between the jaw members, e.g., 110 and 120, and is selectively movable and energizable upon activation of the trigger assembly, a handswitch, etc. It is also envisioned that the "hot wire" may be configured such that the user can move the wire in an inactivated or activated state which as can be appreciated would allow the user to cut the tissue on a reverse stroke if desired. For example, the hot wire may be secured to one jaw member, e.g., 110, and held in friction fit engagement against the other jaw member, e.g., 120, to allow the tissue or vessel to pass between the jaw members 110, 120 when grasping and/or when moving the hot wire in an inactivated state distally. Once sealed, the user retracts the wire while energizing the hot wire to cut the tissue on the reverse stroke.

It is also contemplated that the hot wire may be segmented with each end secured to a respective jaw member 110, 120. This would allow the two opposing hot wires to freely pivot in one direction (i.e., to allow through movement of the tissue between the jaw members 110, 120 in one direction, e.g., upon retraction) and limit the through movement of the tissue in the opposite direction.

In another embodiment, the hot wire may include a hot (i.e., uninsulated) leading edge and an insulated trailing edge which will prevent charring on the return stroke.

Although the subject instrument has been described with respect to preferred embodiments, it will be readily apparent to those having ordinary skill in the art to which it appertains that changes and modifications may be made thereto without departing from the spirit or scope of the subject instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A surgical instrument comprising:
 a drive rod assembly including an elongated hollow shaft portion having a proximal end and a distal end and a central shaft slidably disposed in and axially aligned with the hollow shaft portion;
 a handle assembly coupled to the hollow shaft portion and the central shaft of the drive rod assembly, the handle assembly configured to actuate the drive rod assembly;
 an end effector assembly including a pair of opposing jaw members each being pivotally connected to the central shaft by a pivot pin and each operatively associated with the distal end of the hollow shaft portion, wherein each jaw member includes a jaw housing defining a tissue contacting surface, the jaw housing includes a flange extending therefrom through which pivot pin extends and a flexible cam arm extending proximally from the flange, the flexible cam arms configured to pivot the jaw members about the pivot pin relative to one another between a first position wherein the jaw members are disposed in spaced relation relative to one another and a second position wherein the jaw members are approximated towards one another when the elongated hollow shaft portion is axially displaced relative to the central shaft, and wherein both flexible cam arms are cammed by the hollow shaft portion to move the jaws between the first and second positions and disposed within the hollow shaft portion when the central shaft is moved relative to the hollow shaft portion; and a source of electrical energy connected to each jaw member for conducting energy therebetween.

2. The surgical instrument according to claim 1, further comprising an activator disposed in the handle assembly, the activator having a movable handle and a fixed handle which cooperate to lock and unlock the jaw members.

3. The surgical instrument according to claim 2, further comprising a rotating assembly attached to the handle assembly, the rotating assembly configured to control rotation of the end effector assembly.

4. The surgical instrument according to claim 1, wherein the jaw members are configured to pivot as the elongated hollow shaft portion is axially displaced relative to the central shaft.

5. The surgical instrument according to claim 1, wherein both flexible cam arms are cammed by the hollow shaft portion to move the jaws from an open position to a closed position when the central shaft is moved distally relative to the hollow shaft portion, and wherein both flexible cam arms are cammed by the hollow shaft portion to move the jaws from the closed position to the open position when the central shaft is moved proximally relative to the hollow shaft portion.

6. The surgical instrument according to claim 1, wherein the central shaft further comprises a bifurcated distal end defining a pair of arms and a cavity between the arms for receiving the flanges of jaw members.

7. The surgical instrument according to claim 1, further comprising electrically conductive sealing surfaces disposed on each jaw member, the electrically conductive sealing surfaces being electrically connected to the source of electrical energy.

8. The surgical instrument according to claim 7, wherein each jaw member is electrically isolated from one another.

9. The surgical instrument according to claim 7, wherein the sealing surfaces are coated with a non-stick material.

10. The surgical instrument according to claim 7, wherein at least one of the pair of jaw members is partially constructed of a hard anodized aluminum having a high dielectric strength which electrically isolates the jaw members and confines the electrosurgical energy between the electrically conductive sealing surfaces.

11. The surgical instrument according to claim 7, further comprising a switching mechanism for selecting between a variety of heating technologies.

12. The surgical instrument according to claim 1, wherein the surgical instrument further includes a knife assembly slidably supported in the elongate hollow shaft, the knife assembly being configured and dimensioned to cut tissue grasped between jaw members.

13. The surgical instrument according to claim 1, wherein the cam arms are constructed of a resilient material.

14. The surgical instrument according to claim 1, wherein the jaw members are at least partially constructed of at least one of titanium and stainless steel.

15. The surgical instrument according to claim 1, wherein the cam arm of a first jaw member extends through a first aperture formed in the hollow shaft portion and the cam arm of a second jaw member extends through a second aperture formed in the hollow shaft portion, and wherein proximal displacement of the hollow shaft portion relative to the central shaft results in a distal surface of said apertures engaging a distal surface of said cam arms to move the jaw members to the second position, and wherein distal displacement of the hollow shaft portion relative to the central shaft results in a proximal surface of said apertures engaging a proximal surface of said cam arms to move the law members to the first position.

16. A surgical instrument comprising:

a drive rod assembly including an elongated hollow shaft portion having a proximal end and a distal end and a central shaft slidably disposed in and axially aligned with the hollow shaft portion;

a handle assembly coupled to the hollow shaft portion and the central shaft of the drive rod assembly, the handle assembly configured to actuate the drive rod assembly;

a pair of opposing jaw members each operatively associated with the distal end of the hollow shaft portion, the jaw members being movable relative to one another between an open position wherein the jaw members are disposed in spaced relation relative to one another and a closed position wherein the jaw members are approximated towards one another, wherein each jaw member includes a flexible cam arm extending from a proximal end thereof, the flexible cam arms configured to pivot the jaw members between open and closed positions when the elongated hollow shaft portion is axially displaced relative to the central shaft, wherein both cam arms are cammed by the hollow shaft portion to move the jaws from the open position to the closed position when the central shaft is moved distally relative to the hollow shaft portion, and wherein both flexible cam arms are cammed by the hollow shaft portion to move the jaws from the closed position to the open position when the central shaft is moved proximally relative to the hollow shaft portion; and a source of electrical energy connected to each jaw member for conducting energy therebetween.

17. The surgical instrument according to claim 16, further comprising a knife assembly slidably supported in the elongate hollow shaft, the knife assembly being configured and dimensioned to cut tissue grasped between jaw members.

18. The surgical instrument according to claim 16, further comprising electrically conductive sealing surfaces having a series of stop members, the stop members being configured and dimensioned to facilitate gripping and manipulation of tissue and defining a gap between the jaw members.

19. The surgical instrument according to claim 16, wherein the cam arm of a first jaw member extends through a first aperture formed in the hollow shaft portion and the cam arm of a second jaw member extends through a second aperture formed in the hollow shaft portion, and wherein proximal displacement of the hollow shaft portion relative to the central shaft results in a distal surface of said apertures engaging a distal surface of said cam arms to move the jaw members to the second position, and wherein distal displacement of the hollow shaft portion relative to the central shaft results in a proximal surface of said apertures engaging a proximal surface of said cam arms to move the jaw members to the first position.

* * * * *